United States Patent [19]

Horowitz et al.

[11] Patent Number: 5,514,647
[45] Date of Patent: *May 7, 1996

[54] FIBRONECTIN-CONTAINING OPHTHALMIC SOLUTION, METHOD OF PRESERVING AN OPTHALMIC SOLUTION, AND METHODS OF TREATMENT OF OPTHALMIC WOUNDS

[75] Inventors: Bernard Horowitz, New Rochelle; Richard W. Shulman; Adrianne J. Setton, both of New York, all of N.Y.; Toyohiko Nishimura, Hyogo; Yoichi Kawashima, Kyoto, both of Japan

[73] Assignees: New York Blood Center, Inc., New York, N.Y.; JCR Pharmaceuticals Co., Ltd., Ashiya; Santen Pharmaceutical Co., Ltd., Osaka, both of Japan

[*] Notice: the term of this patent shall not extend beyond the expiration date of Pat. No. 5,348,939.

[21] Appl. No.: 252,366

[22] Filed: Jun. 1, 1994

Related U.S. Application Data

[62] Division of Ser. No. 60,244, May 11, 1993, Pat. No. 5,348,939, which is a continuation of Ser. No. 800,060, Nov. 27, 1991, abandoned.

[51] Int. Cl.$^6$ ..................................................... A61K 37/10
[52] U.S. Cl. ................................................ 514/8; 514/912
[58] Field of Search ........................................... 514/8, 912

[56] References Cited

U.S. PATENT DOCUMENTS

| | | | |
|---|---|---|---|
| 4,565,651 | 1/1986 | Ohmura | 260/112 |
| 4,740,498 | 4/1988 | Hirao et al. | 514/8 |
| 4,837,019 | 6/1989 | Georgalas et al. | 424/101 |
| 4,841,023 | 6/1989 | Horowitz | 530/351 |

FOREIGN PATENT DOCUMENTS

0058993  9/1982  European Pat. Off. .

OTHER PUBLICATIONS

Stern, M. E. et al., "The Effects of Human Recombinant Epidermal Growth Factor on Epithelial Wound Healing," *Healing Processes in the Cornea*, pp. 69–77 (C. E. Crosson and H. E. Kaufman, Eds.) (1989).
Countois, Y. et al., 181 *C R. Soc. Biol.*, pp. 491–495 (1987).
Horowitz, B. and Chang, N. Y., "Preparation of Fibronectin for Therapeutic Administration", *Fibronectin*, pp. 441–455 (Deane S. Mosher, Ed.) (1989).
Moses, R. et al., 18 *Invest Ophthamal* 103–106 (1979).
Nishida, T., et al., 102 *Arch. Opthamal* 455–456 (1984).
Assouline, M. et al., "Fibroblast Growth Factor Effects on Corneal Wound Healing in the Rabbit", *Healing Processes in the Cornea*, pp. 79–97 (C. E. Crosson and H. E. Kaufman, Eds.) (1989).
Mullen, W. et al., Survey of Ophtalmology, 17:469–483 (1973).
Nelson, J. D., et al., Am. J. of Opthal. 114:441–447 (1992).
The *USP*, vol. XXI, p. 1339, "General Information/Pharmaceutical Dosage Forms" 1985.
Chemical Abstracts, vol. 11, No. 10, p. 368, col. 1, Shiseido Co., Ltd., "Cosmetics containing fibronectin" (Sep. 3, 1984).
Gottfried, N. S., "Alkali p–Hydroxybenzoate Esters as Pharmaceutical Preservatives", *Am. J. Hosp. Pharm.*, 19:310–314 (1962).

*Primary Examiner*—Zohreh Fay
*Attorney, Agent, or Firm*—Bryan Cave

[57] ABSTRACT

A stable and soluble multi-dose ophthalmic solution is disclosed. The solution contains fibronectin, an amino acid, a sugar, and a lower alkyl p-hydroxybenzoate. A method treatment of ophthalmic wounds employing the ophthalmic solution, a process for preparing fibronectin for ophthalmic use, a method of lyophilizing an aqueous solution of fibronectin free of albumin, a method for inhibiting bacterial growth in an ophthalmic solution while preserving the cellular adhesion and wound healing activities of fibronectin, and a method of treatment of ophthalmic wounds administering a wound-healing accelerator solution are also disclosed.

12 Claims, No Drawings

FIBRONECTIN-CONTAINING OPHTHALMIC SOLUTION, METHOD OF PRESERVING AN OPTHALMIC SOLUTION, AND METHODS OF TREATMENT OF OPTHALMIC WOUNDS

This is a divisional of U.S. application Ser. No. 08/060,244, filed May 11, 1993, now U.S. Pat. No. 5,348,439 which is a continuation of Ser. No. 07/800,060, filed Nov. 27, 1991, now abandoned.

FIELD OF THE INVENTION

This invention relates to a stable and soluble multi-dose ophthalmic solution containing fibronectin, an amino acid, a sugar, and a lower alkyl p-hydroxybenzoate preservative and to a method of treatment of ophthalmic wounds employing the ophthalmic solution. This invention further relates to a process for preparing fibronectin for ophthalmic use. This invention further relates to a method for inhibiting bacterial growth in an ophthalmic solution while preserving the cellular adhesion and wound healing properties of fibronectin.

BACKGROUND OF THE INVENTION

Fibronectin is useful in therapeutic treatment because of the role that it plays in cellular adhesion, blood coagulation, malignant transformation, reticuloendothelial system function, and embryonic differentiation. Fibronectin's role in cellular adhesion and in promoting epithelial cell outgrowth makes it desirable for treatment of ophthalmic wounds, particularly corneal disorders. Other growth factors have also been identified as being useful as healing accelerators for treatment of ophthalmic wounds. For example, recombinant human epithelial growth factor has been shown to accelerate corneal re-epithelialization following abrasive injury or alkali burn injury (Stern et al., "The Effects of Human Recombinant Epidermal Growth Factor on Epihelial Wound Healing", in *Healing Processes in the Cornea*, at 69–75 (C. E. Crosson and H. E. Kaufman, eds.) (1989). Similarly, fibroblast growth factor has also been reported to stimulate corneal healing (Countois, Y. et al., 181 *C. R. Soc. Biolo*, 491 (1987). Numerous other growth promoting substances have also been identified (e.g., interleukin 6, platelet-derived growth factor, etc.) and may be useful in accelerating ophthalmic wound healing. Ophthalmic wounds can be caused in many ways, for example, by puncture, physical trauma, acid splash, surgical incisions, chemical burns, or lacerations. It is believed that fibronectin promotes the migration of epithelial cells over the wound surface and promotes binding of the epithelial cells to the wound surface to provide a permanent closure of the wound. This process may stimulate the production of endogenous growth factors, such as fibroblast growth factors.

To treat an ophthalmic wound with fibronectin, the fibronectin should be applied by means of an ophthalmic solution. Multi-dose ophthalmic solutions to be used by a single user are the typical mode of applying ophthalmic solutions. One problem in using fibronectin arises from U.S. Federal Food and Drug Agency ("FDA") regulations which require the addition of a preservative to inhibit bacterial growth in a multi-dose ophthalmic solution.

Benzalkonium chloride is the most commonly used preservative in ophthalmic solutions, but it cannot be used with fibronectin because it inhibits the wound healing activity of the fibronectin. Chlorobutanol and phenylethyl alcohol are accepted alternative preservatives in ophthalmic solutions, but they also cannot be used with fibronectin. Chlorobutanol is hydrolyzed in a neutral pH solution. Phenylethyl alcohol cannot be used because it inhibits fibronectin's wound healing activity. Similarly, preservatives made from sodium dehydroacetate or cetylpyridinium dichloride inhibit the wound healing activity of fibronectin. Thimerosal does not inhibit fibronectin's wound healing activity but thimerosal's mercury content and the toxicity problems associated with mercury make it unsuitable for use as a preservative in an ophthalmic solution.

A second difficulty in using fibronectin in ophthalmic settings are problems related to the poor solubility and stability of fibronectin in an aqueous solution. Because of fibronectin's poor storage stability in solution it is a standard practice to lyophilize a solution of fibronectin with a stabilizing agent, usually a neutral amino acid, monosaccharide, disaccharide, or sugar alcohol. A solvent is added to the lyophilized fibronectin just before use. The disadvantage of this method is that the dissolving of the lyophilized preparation in the solvent, typically water, takes a long time and the resulting solution is often turbid because of fibrous insoluble matter.

One method to address this lyophilization problem has been disclosed in Ohmura U.S. Pat. No. 4,565,651. In the Ohmura patent, prior to lyophilization, both albumin and at least one stabilizer selected from neutral amino acids, monosaccharides, disaccharides, and sugar alcohols are added to a fibronectin-containing aqueous solution which is then lyophilized. According to Ohmura, when his lyophilized fibronectin is dissolved in water, the dissolution time is rapid, with little or no turbidity. For an ophthalmic solution, however, the lyophilized fibronectin of Ohmura may prove unacceptable because of the presence of an additional protein, albumin. Albumin renders preservatives less effective and may also interfere with the function of fibronectin. Additionally, the lyophilized fibronectin produced by the method of the Ohmura patent tends to cake up and then does not dissolve easily.

SUMMARY OF THE INVENTION

The present invention provides a stable and readily soluble multi-dose ophthalmic solution containing fibronectin and an anti-microbial preservative.

The present invention further provides a stable and readily soluble single-dose ophthalmic solution containing fibronectin.

The present invention further provides anti-microbial preservatives which do not interfere with the properties of wound healing accelerants.

The present invention also provides a method for treatment of ophthalmic wounds by administering to the wound an ophthalmic solution containing virally sterilized, heterologous fibronectin.

The present invention also provides a process for preparing fibronectin for ophthalmic use comprising lyophilizing an aqueous solution free of albumin and comprising fibronectin as the only protein.

Another advantage of this process is that a lyophilized fibronectin is produced that is free of unnecessary proteins and that, when dissolved, provides a solution that is stable and soluble.

The present invention provides a multi-dose ophthalmic solution containing fibronectin together with a preservative to inhibit bacterial growth.

The present invention enables one to avail oneself of the wound healing activity of virally sterilized, heterologous fibronectin for the treatment of ophthalmic wounds.

The present invention provides an opthalmic solution containing fibronectin in which most, if not virtually all, of the viruses contained therein are inactivated or removed, and in which the structure, function, and activity of fibronectin are maintained.

The present invention also provides a method of obtaining a non-turbid fibronectin solution from lyophilized fibronectin, comprising adding to an aqueous fibronectin solution a sugar and an amino acid, the amount of sugar and the amount of amino acid being sufficient to prevent turbidity when the solution is lyophilized and thereafter dissolved in an aqueous solvent.

The present invention also provides a method for inhibiting bacterial growth while preserving the cellular adhesion and wound healing properties of fibronectin in an opnthalmic solution comprising adding a lower alkyl p-hydroxybenzoate preservative to an ophthalmic solution comprising fibronectin, an amino acid, and a sugar.

DETAILED DESCRIPTION OF THE INVENTION

In the process of the invention, an aqueous solution free of albumin and containing fibronectin, an amino acid, and a sugar, is lyophilized under vacuum. Prior to lyophilization, the fibronectin is present in an amount from 0.25 to 30 mg/ml, preferably 3 mg/ml.

The amino acid may be a water-soluble hydrophilic amino acid such as serine, histidine, alanine, lysine, or glycine. Glycine is the preferred amino acid. The concentration of amino acid in the aqueous solution to be lyophilized is from 0.005 to 1.5M, preferably 0.12M.

The sugar may be a monosaccharide such as glucose, a disaccharide such as sucrose or galactose, a trisaccharide such as a raffinose, a polysaccharide such as dextran, or sugar derivatives such as sorbitol or mannitol, or a combination thereof. Sucrose is the preferred sugar. The concentration of sugar in the aqueous solution to be lyophilized is from 0.005 to 1.5M, preferably 0.30M.

It is most preferred to add a combination of glycine and sucrose to the aqueous solution of fibronectin to be lyophilized. The glycine is present in the solution to be lyophilized in a concentration of from 0.005 to 1.5M, preferably 012M, and the sucrose is present in the solution in a concentration of from 0.005 to 1.5M, preferably 0.30M.

It is preferred to utilize an aqueous solution containing fibronectin which has been treated to inactivate the lipid-enveloped viruses present in the starting biological material. U.S. Pat. No. 4,841,023, and the references incorporated therein, describe a suitable method for the disruption of lipid-containing viruses. Additionally, efficient virus removal occurs with gelatin sepharose chromatography (Horowitz and Chang in *Fibronectin*, at 441–455 (Deane F. Mosher ed.) (1989)).

When the lyophilization is complete, the flask is sealed under vacuum. It is preferred when lyophilization is complete to introduce nitrogen and seal the flask under nitrogen or another non-reactive gas. The solubility of the lyophilized fibronectin is improved when it has been sealed in this manner.

The lyophilized fibronectin obtained from this process is employed in making the ophthalmic solution of the present invention. It is understood that fibronectin obtained by other methods may also be used in the ophthalmic solution of the present invention.

In one embodiment of the invention, the ophthalmic solution comprises fibronectin, an amino acid, a sugar and a solvent. The fibronectin is present in a concentration from 0.25 mg/ml to 10 mg/ml, preferably 1 mg/ml. The amino acid is glycine, serine, histidine, alanine, lysine or other water-soluble hydrophilic amino acids, and mixtures thereof, preferably glycine, and is present in a concentration of from 0.005 to 0.5M, preferably 0.04M. The sugar is a monosaccharide such as glucose, a disaccharide such as sucrose or galactose, a trisaccharide such as a raffinose, a polysaccharide such as dextran, or sugar derivatives such as sorbitol or mannitol, or a combination thereof, preferably sucrose, and is present in a concentration of from 0.005 to 0.5M, preferably 0.1M. It is most preferred that the amino acid be glycine and the sugar be sucrose. The solvent may be sterile water, U.S.P. Grade Purified Water, or a neutral physiological buffer, such as phosphate buffered saline ("PBS"). It is preferred to use U.S.P. water as the solvent.

Sodium chloride may optionally be added to the ophthalmic solution in a concentration from 0.01 to 0.2M, and is preferably 0.087M.

In another embodiment, the ophthalmic solution also contains a preservative. The preservative is a lower alkyl p-hydroxybenzoate which is commonly referred to as "Parabens" or by the designation "PB". Preferred lower alkyl p-hydroxybenzoate preservatives are methyl p-hydroxybenzoate ("methyl paraben"), ethyl p-hydroxybenzoate ("ethyl paraben"), propyl p-hydroxybenzoate ("propyl paraben"), butyl p-hydroxybenzoate ("butyl paraben"), and mixtures thereof. The preservative is desirably in the form of an aqueous solution at a concentration from 0.002 to 0.25% (w/v). The water used in the aqueous solution may be U.S.P. Grade Purified Water, sterile water, or water purified by conventional techniques.

It is preferred to add two of the lower alkyl p-hydroxybenzoate preservatives to the ophthalmic solution. The preferred combinations of preservatives are:

1. Ethyl p-hydroxybenzoate in a concentration from 0.005 to 0.17% (w/v), preferably 0.02% (w/v), and butyl p-hydroxybenzoate in a concentration from 0.002 to 0.021% (w/v), preferably 0.01% (w/v); or 2. Methyl p-hydroxybenzoate in a concentration from 0.012 to 0.25% (w/v), preferably 0.038% (w/v), and propyl p-hydroxybenzoate in a concentration from 0.005 to 0.05% (w/v), preferably 0.015% (w/v).

In another embodiment, a potentiating agent is added in order to improve the efficacy of the preservative or preservatives in the ophthalmic solution. The potentiating agent is preferably ethylenediaminetetraacetic acid ("EDTA") or a salt thereof, preferably disodium ethylenediaminetetraacetate or disodium dihydrate ethylenediaminetetraacetate ($Na_2C_{10}H_{14}O_8N_2 \cdot 2H_2O$). The preferred potentiating agent is disodium dihydrate ethylenediaminetetraacetate. The potentiating agent is added to the ophthalmic solution in a concentration from 0.005 to 0.1% (w/v). When disodium dihydrate EDTA is used, the concentration is preferably 0.01% (w/v).

Ophthalmic wounds, and in particular, cornell disorders may be treated by administering the ophthalmic solution of the present invention in an amount effective to treat the wound and to promote wound healing. The amount of the ophthalmic solution that will be required for the treatment will depend upon the nature and scope of the ophthalmic wound. Suggested dosages are one drop applied to the eye four times per day during waking hours up to eight weeks or 56 days.

The invention is further illustrated by the following examples:

EXAMPLE 1

A. FORMULATION OF FIBRONECTIN EYE DROPS

Virus inactivated purified fibronectin (Horowitz and Chang, in *Fibronectin*, at 441–455 (Deane F. Mosher ed.) (1989)) in PBS is formulated to produce a 1.0 ml solution containing 3.0 mg fibronectin, 0.30M sucrose, 0.12M glycine, 0.262M sodium chloride and 0.03M sodium phosphate buffer, pH 7.4

An aliquot of purified fibronectin containing 3 mg fibronectin is added to 0,339 gm of a 1.0M sucrose solution, 0.300 gm of a solution containing 0.09M sodium phosphate buffer, 0.715M sodium chloride, 0.4M glycine, pH 7.4 and sufficient PBS (0.01M sodium phosphate buffer, 0.12M sodium chloride, pH 7.4) to bring the mixture to 1,039 gm or 1.0 ml.

The mixture is filtered using a Pall, nylon, 0.2 micron filter (Pall Corp., NY, N.Y.) and 1 ml filled into sterile, 6 ml glass vials. A sterile 20 mm, siliconized, 890 grey butyl lyophilization split stopper (West Corp.) is inserted partway into the vial neck and the vials placed into a stainless steel-covered lyophilization box. The vials are frozen at $-50°$ to $-70°$ C. prior to lyophilization.

Following lyophilization, the fibronectin is dissolved with 3 ml of sterile U.S.P. Grade Purified Water containing 0.02% ethyl paraben, 0.01% butyl paraben and 0.01% disodium dihydrate ethylenediaminetetraacetate.

B. LYOPHILIZATION OF FIBRONECTIN EYE DROPS

The formulated, vialed fibronectin is frozen at $-50°$ to $-70°$ C. The lyophilization initiates with the shelf temperature at $\leq -45°$ C. and the chamber at a pressure of $\leq 100$ microns mercury. The fibronectin is held at these conditions for approximately 2 hours after which the shelf temperature is raised to between $-20°$ and $-10°$ C. with the pressure at <100 microns. When the product temperature begins to rise, the shelf temperature is raised to 10° C. above the product temperature. As the product temperature rises the shelf temperature is raised to maintain a constant 10° C. differential between the two. The pressure is maintained at <100 microns.

After the product temperature reaches a final temperature of 20° to 35° C. the shelf temperature is held to maintain the final temperature. The product is held at the final temperature for 20.5 to 45.5 hours at a pressure of <100 microns.

Lyopnilization is terminated by stoppering under a pressure of <100 microns, or after backfilling with nitrogen gas to a pressure of approximately one inch of water.

The moisture content typically is between 0.3 and 3% (w/v).

EXAMPLE 2

Preparation of Fibronectin-Containing Ophthalmic Solution

An ophthalmic solution was prepared in accordance with the following procedure. The solution was prepared by combining fibronectin lyophilized according to Example 1 with 3 ml of a sterile solution containing 0.01% butyl p-hydroxybenzoate, 0.02% propyl p-hydroxybenzoate, and 0.01% disodium dihydrate ethylenediaminetetraacetic acid $(Na_2C_{10}H_{14}O_8N_2 \cdot 2H_2O)$ in U.S.P. Grade Purified Water. The solution is provided from an eyedropper bottle. The procedure is as follows: The stopper is removed from the vial containing the lyophilized fibronectin; the eyedropper bottle cap is unscrewed; the vial is snapped onto the top of the eyedropper bottle; the solution is added to the fibronectin vial by inverting; the solution is swirled if necessary; the solution is reinverted into the eyedropper bottle; the fibronectin vial is removed from the top of the eyedropper bottle; the eyedropper bottle cap is screwed on tightly; the final solution is swirled gently to ensure a homogeneous solution. A fully soluble solution is typically reached in $\leq 1$ minute. The final ophthalmic solution contains the following components in the quantities indicated:

| Component | Quantity |
|---|---|
| Fibronectin | 1 mg/ml |
| Sodium Phosphate Buffer (pH 7.4) | 0.01M |
| Sucrose | 0.1M |
| Glycine | 0.04M |
| Sodium Chloride | 0.087M |
| Butyl p-hydroxybenzoate | 0.01% |
| Ethyl p-hydroxybenzoate | 0.02% |
| Disodium dehydrate ethylenediaminetetraacetic acid | 0.01% |

When the ophthalmic solution is intended for the individual use of one patient, the solution may be packaged in sterile multiple-dose containers which are sealed and made tamper-proof.

EXAMPLE 3

Effect of Parabens Preservative on Cell Binding Activity of Fibronectin

An ophthalmic solution with a fibronectin concentration of 1.197 mg/ml was prepared in phosphate buffered saline ("PBS") with the Parabens preservative being a combination of 0.05% methyl p-hydroxybenzoate and 0.015% propyl p-hydroxybenzoate (Sample 1). A second ophthalmic solution with a fibronectin concentration of 1.197 mg/ml was prepared in PBS without adding a preservative (Sample 2). Samples 1 and 2 were allowed to stand at room temperature for seven days.

A fibronectin standard of 10 mg fibronectin/ml in PBS was diluted in triplicate with PBS (NaCl 8,000 mg, KCl 200 mg, $Na_2HPO_4$ 1,150 mg, $KH_2PO_4$ 200 mg in 1 liter of double distilled water, pH 7.3) to make dilution series of 5,000 to 0.078 ug/ml of fibronectin standard. Sample 1 and 2 were each diluted in triplicate with PBS to make dilution series for each sample of 5.000 to 0.078 ug/ml of fibronectin.

The cell binding activity of fibronectin was measured using a BHK cell attachment assay in accordance with the following procedure. A 96-well microplate was precoated with 200 ul of 3% BSA (30 mg/ml of BSA in PBS) at 37° C. for 2 hours and rinsed twice with 100 ul of PBS. Fifty (50) ul of each dilution of the reference fibronectin and the test samples (Sample 1 and Sample 2) were transferred into separate wells of the 96-well microplate. The plate was incubated at 37° C. for 60 minutes and the dilutions discarded by aspiration. One hundred (100) ul of 3% BSA were added into each well and the plate incubated for 60 minutes at 37° C. During this incubation, a BHK cell suspension was prepared as follows: BHK cells, cultured in RPMI-1640 media containing 10% fetal bovine serum, were scraped from a tissue culture plate with a cell scraper and centrifuged at 1,000 rpm for 7 minutes. The cell plate was suspended in serum free RPMI- 1640 media (RMPI-1640 supplemented with 20 mM HEPES) and centrifuged at 1,000 rpm for 7 minutes. This step was then repeated, to further wash the BHK cells. The washed BHK cells were resuspended in serum free RPMI-1640 media and a single cell suspension generated by pipetting. The cell number was adjusted to $2 \times 10^6$ cells/ml with serum free RPMI-1640. The 96-well plate was then rinsed twice with 100 ul PBS. Fifty (50) ul of the BHK cell suspension were added to each separate well of the 96-well plate. The plate was incubated at 37° C. in a 5% $CO_2$ incubator for 90 minutes. The cell suspension was discarded by aspiration and the plate rinsed with 100 ul of saline. Fifty (50) ul of E-MEM medium (Eagle's MEM supplemented with 5% FBS) were added into each well of the assay plate. Fifty (50) ul of Neutral Red solution was added into each well of the assay plate. (The Neutral Red solution was prepared by adding 2 ml of 1 m HEPES and 10 ml of 1% neutral to 88 mls of E-MEM medium just prior to use). The plate was incubated at 37° in a 5% $CO_2$ incubator for 60 minutes. The plate was rinsed twice with 100 ul of saline and 200 ul of Neutral Red Extraction Buffer (0.05M solution phosphate monobasic in 50% EtOH) was added to each well of the plate. The plate was left standing at room temperature overnight and the absorbance of each well was then read spectrophotometrically at 546 nm.

The fibronectin content in mg/ml of each dilution of the dilution series for Sample 1 and Sample 2 was determined in comparison to the reference fibronectin standard. The data obtained was used to calculate the relative potencies of Sample 1 and Sample 2 against the fibronectin sample by parallel line assay. The cell binding activity for each test, the mean, and the standard deviation (S.D.) are presented below in Table I.

TABLE I

|  | Test 1 | Test 2 | Test 3 | Mean | S.D. |
|---|---|---|---|---|---|
| Sample 1 | 1.229 | 1.198 | 1.257 | 1.228 | 0.030 |
| Sample 2 | 1.182 | 1.133 | 1.140 | 1.152 | 0.027 |

There was no significant difference in the cell binding activity of Sample 1 and Sample 2 as shown by the results in Table I. This demonstrates that the Parabens preservative did not affect the cell binding activity of fibronectin in an ophthalmic solution.

EXAMPLE 4

Effect of Different Parabens Preservatives on Cell Binding Activity of Fibronectin An ophthalmic solution was prepared according to the procedure of Example 2, except that the Parabens preservative was a combination of 0.02% ethyl p-hydroxybenzoate and 0.01% butyl p-hydroxybenzoate, and the concentration of disodium ethylenediaminetetraacetate (in sterile water) was 0.05% (Sample 1). Sample 1 was divided into four parts (Samples 1A, 1B, 1C, and 1D). Sample 1A was stored at 4° C. for 7 days. Sample 1B was stored at 4° C. for 14 days. Sample 1C was stored at 37° C. for 7 days. Sample 1D was stored at 37° C. for 14 days.

A second ophthalmic solution was prepared according to the procedure of Example 2, except that the Parabens preservative was a combination of 0.038% methyl p-hydroxybenzoate and 0.015% propyl p-hydroxybenzoate, and the concentration of disodium ethylenediaminetetraacetate (in sterile water) was 0.05% (Sample 2). Sample 2 was divided into four parts (Samples 2A, 2B, 2C and 2D). Sample 2A was stored at 4° C. for 7 days. Sample 2B was stored at 4° C. for 14 days. Sample 2C was stored at 37° C. for 7 days. Sample 2D was stored at 37° C. for 14 days.

The cell binding activity of fibronectin was measured using a standard BHK cell attachment assay in accordance with the procedure described in Example 3. A fibronectin standard of 1.0 mg fibronectin/ml of PBS, stored at −80° C., was diluted with PBS to make a control dilution series of 5.000 to 0.078 ug/ml of fibronectin standard. On day 7, Samples 1A and 1C and Samples 2A and 2C were each diluted with PBS to make a dilution series for each sample of 5.000 to 0.078 ug/ml of sample. The BHK cell attachment assay was performed on each dilution series for Samples 1A and 1C, Samples 2A and 2C, and the fibronectin standard and the fibronectin content in mg/ml of each dilution was determined. On day 14, the dilution series procedures and the BHK cell attachment assays were performed on the dilution series for Samples 1B and 1D, Samples 2B and 2D, and the fibronectin standard. The data obtained was then used to calculate by parallel line assay the relative potencies of Samples 1A-D and Samples 2A-D against the fibronectin standard. The assay was repeated four more times for each sample. Table II below presents the cell binding activity results of these assays as an average of the five assays and the standard deviation (±S.D.).

TABLE II

| Sample # | Storage (°C.) | # Days Storage | Fibronectin (mg/ml) | Activity (%) |
|---|---|---|---|---|
| Control | −80 | (—) | 1.090 ± 0.72 | 100.0 ± 6.6 |
| 1A | 4 | 7 | 1.027 ± 0.025 | 94.2 ± 2.3 |
| 1B | 4 | 14 | 1.131 ± 0.045 | 103.8 ± 4.1 |
| 1C | 37 | 7 | 1.083 ± 0.053 | 99.4 ± 4.9 |
| 1D | 37 | 14 | 1.059 ± 0.024 | 97.2 ± 2.2 |
| 2A | 4 | 7 | 1.094 ± 0.027 | 100.4 ± 2.5 |
| 2B | 4 | 14 | 1.094 ± 0.036 | 100.4 ± 3.3 |
| 2C | 37 | 7 | 1.158 ± 0.048 | 106.2 ± 4.4 |
| 2D | 37 | 14 | 1.090 ± 0.069 | 100.0 ± 6.3 |

There was no significant difference in the cell binding activity of Sample 1 and Sample 2, whether stored for 7 days or 14 days, or stored at room temperature or under refrigeration, as shown by the results in Table II. This demonstrates that Parabens preservatives together with disodium ethylenediaminetetratacetic acid did not affect the cell binding activity or stability of fibronectin in ophthalmic solutions.

EXAMPLE 5

Effect of Parabens Preservative On Gelatin Binding Activity of Fibronectin

An ophthalmic solution with a fibronectin concentration of 1.0 mg/ml was prepared in PBS, with the Parabens preservative being a combination 0.05% methyl p-hydroxybenzoate and 0.015% propyl p-hydroxybenzoate (Sample 1). A second ophthalmic solution with a fibronectin concentration of 1.0 mg/ml was prepared in PBS without adding a preservative (Sample 2). Samples 1 and 2 were allowed to stand at room temperature for seven days.

The gelatin binding activity of fibronectin was measured by gelatin-Sepharose affinity chromatography. First, Sample 1 was subjected onto a GPC-HPLC system (Asahipak GS 710, BioRad 402T HRLC system), the Parabens preservative eliminated, and protein fractions collected. Sample 2 was similarly subjected onto a GPC-HPLC system and protein fractions collected. The collected protein fractions of Sample 1 and Sample 2 were respectively subjected to gelatin-Sepharose chromatography, specifically the gelatin-Sepharose in HR5/5, BioRad 402T, Affinity Chromatography system. The gelatin binding activity of fibronectin was determined by measuring retention time in minutes and the elution peak area of fibronectin. The elution peak area was measured spectrophotometrically at a wavelength of 280 nm. The gelatin binding activity results are presented below in Table III.

TABLE III

|  | Retention Time (min) | Elution Peak Area (280 nm) |
|---|---|---|
| Sample 1 | 42.92 | 345.357 |
| Sample 2 | 42.97 | 342.332 |

There was no significant difference in the gelatin binding activity of Sample 1 and Sample 2, as shown by the results in Table III. This demonstrates that the Parabens preservative did not affect the gelatin binding activity of fibronectin in an ophthalmic solution.

EXAMPLE 6

Effect of Parabens Preservative On Bacteria Binding Activity of Fibronectin

An ophthalmic solution with a fibronectin concentration of 1.0 mg/ml was prepared in PBS, with the Parabens preservative being a combination of 0.05% methyl p-hydroxybenzoate and 0.015% propyl p-hydroxybenzoate (Sample 1). A second ophthalmic solution with a fibronectin concentration of 1.0 mg/ml was prepared in PBS without adding a preservative (Sample 2). Samples 1 and 2 were allowed to stand at room temperature for seven days.

The bacteria binding activity of fibronectin was measured by observing the agglutination after incubation of the ophthalmic solution with a heat-treated *Staphylococcus aureus* solution. The *S. aureus* solution was prepared by diluting *S. aureus* in PBS to a concentration of approximately $1 \times 10^9$ cells/ml, then heating the solution to 100° C. for 10 minutes. Samples 1 and 2 were diluted with PBS to make a dilution series for each sample from 1,000 to 0.2 ug/ml. Using a 24-well microtiter cell culture assay plate, 500 ul of each dilution of Sample 1 and Sample 2 were dispensed into individual wells in the assay plate. Subsequently into each well, 50 ul of *S. aureus* solution was added. At room temperature, the solutions were repeatedly mixed by gently shaking the assay plate every 5 minutes up to one hour. The presence or absence of an agglutinating clump of fibronectin and *S. aureus* bacteria was observed and noted for each dilution of each test sample. The bacteria binding activity results are presented below in TABLE IV.

TABLE IV

| Concentration of Fibronectin in Sample (ug/ml) | Sample 1 | Sample 2 |
|---|---|---|
| 1,000 | ++ | ++ |
| 500 | ++ | ++ |
| 200 | ++ | ++ |
| 100 | ++ | ++ |
| 50 | ++ | ++ |
| 20 | ++ | ++ |
| 10 | + | + |
| 5 | + | + |
| 2 | + | + |
| 1 | ± | ± |
| 0.5 | − | − |
| 0.2 | − | − |
| 0.1 | − | − |
| 0 | − | − |

++: Intense clumping
+: Clumping
±: Weak clumping
−: No clumping

Clumping by fibronectin for both samples was observed when the concentration of fibronectin exceeded 1 ug/ml. No differences in the bacteria-binding activity were observed between Sample 1 and Sample 2 as shown by the results in Table IV. This demonstrates that the Parabens preservative did not affect the bacteria-binding activity of fibronectin in an ophthalmic solution.

EXAMPLE 7

Minimum Inhibitory Concentration of Parabens Preservatives

Ophthalmic solutions were prepared in accordance with the procedure of Example 2 with the following variables indicated in the tables below. The type and concentration of Parabens Preservative was varied. The Parabens preservatives used were methyl paraben ("Mp"), propyl paraben ("Pp"), ethyl paraben ("Ep"), and butyl paraben ("Bp"). Disodium ethylenediaminetetraacetic acid ("EDTA") was added and the concentration of EDTA was varied to test the potentiating effect of EDTA on the Parabens preservatives. These different formulations were separately challenged with an inoculum of *P. aeruginosa* or *C. albicans*. At 6 hours and 24 hours, the inoculated formulations were streaked onto individual culture plates and examined for growth. Growth, indicated by colony forming units, was scored on a scale of 0–4, with 0 indicating no growth to 4 indicating highest growth. The minimum inhibitory concentrations ("MIC") of the Parabens preservatives and the potentiating effects of EDTA on the Parabens preservatives are presented below in Tables V to X.

TABLE V

| MIC Results of Ophthalmic Solution Containing Mp, Pp, and EDTA | | | | | | |
|---|---|---|---|---|---|---|
| | | | P. aeruginosa | | C. albicans | |
| % Mp | % Pp | % EDTA | 6 hrs | 24 hrs | 6 hrs | 24 hrs |
| 0.068 | 0.027 | 0.089 | 1 | 0 | 2 | 0 |
| 0.051 | 0.020 | 0.067 | 2 | 0 | 0 | 0 |
| 0.038 | 0.015 | 0.05 | 2 | 1 | 1 | 1 |
| 0.029 | 0.011 | 0.038 | 2 | 2 | 1 | 1 |
| 0.021 | 0.008 | 0.028 | 2 | 2 | 1 | 1 |
| 0.016 | 0.006 | 0.021 | 2 | 3 | 1 | 1 |

TABLE V-continued

MIC Results of Ophthalmic Solution Containing
Mp, Pp, and EDTA

| % Mp | % Pp | % EDTA | P. aeruginosa 6 hrs | 24 hrs | C. albicans 6 hrs | 24 hrs |
|---|---|---|---|---|---|---|
| 0.012 | 0.005 | 0.016 | 3 | 3 | 1 | 1 |

TABLE VI

MIC Results of Ophthalmic Solution Containing
Mp, Pp, and 0.05% EDTA

| % Mp | % Pp | P. aeruginosa 6 hrs | 24 hrs | C. albicans 6 hrs | 24 hrs |
|---|---|---|---|---|---|
| 0.068 | 0.027 | 1 | 0 | 1 | 0 |
| 0.051 | 0.020 | 2 | 0 | 0 | 0 |
| 0.038 | 0.015 | 2 | 1 | 0 | 0 |
| 0.029 | 0.011 | 3 | 2 | 0 | 0 |
| 0.021 | 0.008 | 3 | 2 | 0 | 0 |
| 0.016 | 0.006 | 4 | 3 | 2 | 1 |
| 0.012 | 0.005 | 4 | 3 | 2 | 1 |

TABLE VII

MIC Results Of Ophthalmic Solution Containing
Mp, Pp, But No EDTA

| % Mp | % Pp | P. aeruginosa 6 hrs | 24 hrs | C. albicans 6 hrs | 24 hrs |
|---|---|---|---|---|---|
| 0.068 | 0.027 | 1 | 0 | 0 | 0 |
| 0.051 | 0.020 | 3 | 1 | 1 | 0 |
| 0.038 | 0.015 | 3 | 2 | 1 | 0 |
| 0.029 | 0.011 | 3 | 3 | 1 | 0 |
| 0.021 | 0.008 | 3 | 3 | 3 | 1 |
| 0.016 | 0.006 | 3 | 3 | 3 | 1 |
| 0.012 | 0.005 | 3 | 3 | 3 | 1 |

TABLE VIII

MIC Results of Ophthalmic Solution Containing
Ep, Bp, and EDTA

| % Ep | % Bp | % EDTA | P. aeruginosa 6 hrs | 24 hrs | C. albicans 6 hrs | 24 hrs |
|---|---|---|---|---|---|---|
| 0.027 | 0.013 | 0.067 | 0 | 0 | 0 | 0 |
| 0.020 | 0.01 | 0.05 | 1 | 0 | 0 | 0 |
| 0.015 | 0.007 | 0.038 | 2 | 1 | 0 | 0 |
| 0.011 | 0.006 | 0.028 | 3 | 2 | 0 | 0 |
| 0.008 | 0.004 | 0.021 | 3 | 3 | 0 | 0 |
| 0.006 | 0.003 | 0.016 | 3 | 3 | 2 | 2 |
| 0.005 | 0.002 | 0.012 | 3 | 4 | 4 | 2 |

TABLE IX

MIC Results of Ophthalmic Solution Containing
Ep, Bp, and 0.05% EDTA

| % Ep | % Bp | P. aeruginosa 6 hrs | 24 hrs | C. albicans 6 hrs | 24 hrs |
|---|---|---|---|---|---|
| 0.027 | 0.013 | 0 | 0 | 0 | 0 |
| 0.020 | 0.010 | 1 | 0 | 1 | 0 |
| 0.015 | 0.007 | 2 | 1 | 1 | 0 |
| 0.011 | 0.006 | 3 | 2 | 1 | 0 |
| 0.008 | 0.004 | 3 | 3 | 1 | 0 |
| 0.006 | 0.003 | 3 | 3 | 1 | 1 |
| 0.005 | 0.002 | 4 | 3 | 1 | 1 |

TABLE X

MIC Results of Ophthalmic Solution Containing
Ep, Bp, But No EDTA

| % Ep | % Mp | P. aeruginosa 6 hrs | 24 hrs | C. albicans 6 hrs | 24 hrs |
|---|---|---|---|---|---|
| 0.027 | 0.013 | 0 | 0 | 0 | 0 |
| 0.020 | 0.010 | 2 | 1 | 1 | 0 |
| 0.015 | 0.007 | 2 | 2 | 1 | 0 |
| 0.011 | 0.006 | 3 | 2 | 1 | 0 |
| 0.008 | 0.004 | 3 | 3 | 1 | 0 |
| 0.006 | 0.003 | 4 | 3 | 1 | 0 |
| 0.005 | 0.002 | 4 | 3 | 2 | 0 |

A preservative made from a combination of methyl paraben in a concentration from 0.012 to 0.068% and propyl paraben in a concentration from 0.005 to 0.027% inhibited the growth of microbes in the ophthalmic solution, as shown in Tables V to VII. The efficacy of this preservative in inhibiting microbial growth was improved when a potentiating agent, EDTA, was added, as shown by a comparison of Tables V and VI with Table VII.

A preservative made from a combination of ethyl paraben in a concentration from 0.005 to 0.027% and butyl paraben in a concentration from 0.002 to 0.013% inhibited the growth of microbes in the ophthalmic solutions, as shown in Tables VIII to X. The efficacy of this preservative in inhibiting microbial growth was improved when a potentiating agent, EDTA, was added, as shown by a comparison of Tables VIII and IX with Table X.

This demonstrates that Parabens preservatives inhibit microbial growth in an ophthalmic solution.

EXAMPLE 8

Effect of Parabens Preservative On Corneal Wound Closing Activity of Fibronectin An ophthalmic solution with a fibronectin concentration of 1.0 mg/ml was prepared in PBS, with the Parabens preservative being a combination of 0.05% methyl p-hydroxybenzoate and 0.015% propyl p-hydroxybenzoate (Sample 1). A second ophthalmic solution with a fibronectin concentration of 1.0 mg/ml was prepared in PBS without adding a preservative (Sample 2). Samples 1 and 2 were allowed to stand at room temperature for seven days. A control ophthalmic solution free of fibronectin and preservative was also prepared.

The corneal wound closing activity of fibronectin was measured following the procedures described in Moses et al., 18 *Invest. Ophthalmol* 103–106 (1979), and Nishida et al., 102 *Arch. Ophthalmol.* 455–456 (1984). Rabbit corneal epithelium was injured by iodine vapor treatment for 3 minutes. Samples 1 and 2 and the control were applied to 27 injured rabbit corneal epithelium samples apiece. One drop of the ophthalmic solution being tested was applied to the injured corneal epithelium at 4, 5, 6, and 7 hours after injury, and at every hour from 16 to 30 hours after injury. At 4, 16, 20, 24, 28, and 32 hours after the iodine treatment, the rabbit corneas were stained with 2% fluorescein and photographed. The stained area of the corneal epithelium was measured by a computerized image analyzer. The healing rate of each corneal wound was calculated by a linear regression of the wound area during the period of 16 to 32 hours after injury by the iodine treatment. The Student's t test was employed. The rabbits that did not have enough corneal epithelium defect at 4 hours after the iodine treatment were excluded by Smirnov's method. The corneal wound healing activity results are presented below in Table XI.

TABLE XI

| | Healing Rate 16–32 hr, mm²/hr | Student's t test (p value) | No. of eyes |
|---|---|---|---|
| Sample 1 | 1.80 ± 0.07 | p < 0.001 | 27 |
| Sample 2 | 1.66 ± 0.05 | p < 0.005 | 27 |
| Control | 1.40 ± 0.05 | — | 27 |

Healing Rate: Mean ± SEM

There was no significant difference in the corneal wound healing activity of Sample 1 and Sample 2 as shown by the results in Table XI. This test demonstrates that the Parabens preservative did not affect the corneal wound healing activity of fibronectin in an ophthalmic solution.

EXAMPLE 9

Effect of Different Parabens Preservatives on Corneal Wound Closing Activity of Fibronectin An ophthalmic solution was prepared in PBS with the Parabens preservative being a combination of 0.02% ethyl p-hydroxybenzoate and 0.01% butyl p-hydroxybenzoate, and the concentration of disodium ethylenediaminetetraacetate was 0.01% (Sample 1).

A second ophthalmic solution with a fibronectin concentration of 0.5 mg/ml was prepared in PBS with the Parabens preservative being a combination of 0.02% ethyl p-hydroxybenzoate and 0.01% butyl p-hydroxybenzoate, and the concentration of disodium ethylenediaminetetraacetate was 0.01% (Sample 2).

A third ophthalmic solution was prepared in PBS, with the Parabens preservative being a combination of 0.038% methyl p-hydroxybenzoate and 0.015% propyl p-hydroxybenzoate, and the concentration of disodium ethylenediaminetetraacetate was 0.05% (Sample 3).

A fourth ophthalmic solution with a fibronectin concentration of 0.5 mg/ml was prepared in PBS, with the Parabens preservative being a combination of 0.038% methyl p-hydroxybenzoate and 0.015% propyl p-hydroxybenzoate, and the concentration of disodium ethylenediaminetetraacetate was 0.05% (Sample 4).

Samples 1–4 were allowed to stand at room temperature for seven days.

The corneal wound closing activity of fibronectin was measured following the procedures described in Moses et al., 18 Invest. Ophthalmol. 103–106 (1979), and Nishida et al., 102 Arch. Ophthalmol. 455–456 (1984). Rabbit corneal epithelium was injured by iodine vapor treatment for 3 minutes. Samples 1–4 and the control were applied to 12 injured rabbit corneal epithelium samples apiece. One drop of the ophthalmic solution being tested was applied to the injured corneal epithelium at 4, 5, 6, and 7 hours after injury, and at every hour from 16 to 30 hours after injury. At 4, 16, 20, 24, 28, and 32 hours after the iodine treatment, the rabbit corneas were stained with 2% fluorescein and photographed. The stained area of the corneal epithelium was measured by a computerized image analyzer. The healing rate of each corneal wound was calculated by a linear regression of the wound area during the period of 16 to 32 hours after injury by the iodine treatment. The rabbits that did not have enough corneal epithelium defect at 4 hours after the iodine treatment were excluded by Smirnov's method. The corneal wound healing activity results are presented below in Table XII.

TABLE XII

| | Concentration of Fibronectin (mg/ml) | Healing Rate 16–32 hr, mm²/hr |
|---|---|---|
| Sample 1 | 1.0 | 1.73 ± 0.08 |
| Sample 2 | 0.5 | 1.36 ± 0.08 |
| Sample 3 | 1.0 | 1.72 ± 0.05 |
| Sample 4 | 0.5 | 1.56 ± 0.12 |

Healing Rate: Mean ± SEM

There was no significant difference in the corneal wound healing activity of Sample 1 versus Sample 3 and Sample 2 versus Sample 4 as shown by the results in Table XII. Moreover, the rate of healing of Samples 1 and 3 was comparable to the rate of healing of Samples 1 and 2 in Example 8. This demonstrates that the different Parabens preservatives did not differentially affect the corneal wound healing activity of fibronectin in an ophthalmic solution.

EXAMPLE 10

Solubility of Fibronectin Lyophilized in the Presence of Sucrose Without Glycine Fibronectin at a concentration of 5 mg/ml in PBS was lyophilized with either 0.05M or 0.1M sucrose. The degree of solubilization of the lyophilized fibronectin was determined by absorbance at 280 nm 10 minutes after reconstitution with distilled water. Based on soluble protein, the present solubility was 66% and 71%, respectively.

EXAMPLE 11

Effect of Sucrose Concentration on the Solubility of Lyophilized Fibronectin in the Presence of Glycine Fibronectin was lyophilized as in Example 1, except that the sucrose concentration was adjusted such that, after reconstitution, the concentration of sucrose in each of the five samples was as given in Table XIII below. After standing at room temperature for 30 minutes, each sample was dissolved in 3 ml of water. All samples completely dissolved, and the time in seconds to complete dissolution of the fibronectin was measured and is shown in Table XIII.

TABLE XIII

| Sucrose Concentration (M) | Time to Complete Dissolution (Seconds) |
|---|---|
| 0.05 | 75–80 |

TABLE XIII-continued

| Sucrose Concentration (M) | Time to Complete Dissolution (Seconds) |
| --- | --- |
| 0.075 | 45–50 |
| 0.10 | 20–25 |
| 0.125 | 20–25 |
| 0.107 | 25–30 |

When fibronectin is lyophilized in the presence of sucrose and glycine, the fibronectin is completely soluble, whereas when lyophilized in the presence of sucrose only, fibronectin is partially soluble as shown in Example 10. The rate of solubility of fibronectin is dependent upon the concentration of sucrose as shown by the results in Table XIII.

It will be understood that various modifications may be made without departing from the spirit of the present invention.

We claim:

1. A method of treatment of ophthalmic wounds comprising administering to the wound a wound healing accelerator solution disposed in a multi-use container, wherein said solution comprises a wound healing accelerator, wherein the wound healing accelerator is fibronectin, epithelial growth factor, or fibroblast growth factor, and a lower alkyl p-hydroxybenzoate preservative, and said wound healing accelerator solution is free of albumin.

2. The method of claim 1, wherein the ophthalmic solution further comprises a potentiating agent selected from the group consisting of ethylenediaminetetraacetic acid and salts thereof.

3. The method of claim 2, wherein the lower alkyl p-hydroxybenzoate preservative comprises a combination of ethyl p-hydroxybenzoate and butyl p-hydroxybenzoate, together with disodium dihydrate ethylenediaminetetraacetate.

4. An ophthalmic solution for application to ophthalmic wounds comprising a wound healing accelerator and a lower alkyl p-hydroxybenzoate preservative, wherein the wound healing accelerator is fibronectin, epithelial growth factor, or fibroblast growth factor, said ophthalmic solution being free of albumin.

5. The ophthalmic solution of claim 4, wherein the lower alkyl p-hydroxybenzoate preservative is from 0.002 to 0.25 % (w/v).

6. The ophthalmic solution of claim 4, wherein the lower alkyl p-hydroxybenzoate preservative comprises methyl p-hydroxybenzoate, ethyl p-hydroxybenzoate, propyl p-hydroxybenzoate, butyl p-hydroxybenzoate, or mixtures thereof.

7. The ophthalmic solution of claim 4, wherein the wound healing accelerator is fibronectin and the concentration of fibronectin is from 0.25 to 10.0 mg/ml.

8. The ophthalmic solution of claim 4, further comprising a potentiating agent selected from the group consisting of ethylenediaminetetraacetic acid and salts thereof.

9. The ophthalmic solution of claim 8, wherein the salts of ethylenediaminetetraacetic acid comprise disodium ethylenediaminetetraacetate and disodium dihydrate ethylenediaminetetraacetate.

10. The ophthalmic solution of claim 8, wherein the lower alkyl p-hydroxybenzoate preservative comprises a combination of ethyl p-hydroxybenzoate and butyl p-hydroxybenzoate, together with disodium dihydrate ethylenediaminetetraacetate.

11. The ophthalmic solution of claim 10, wherein the concentration of ethyl p-hydroxybenzoate is from 0.005 to 0.17 %, the concentration of butyl p-hydroxybenzoate is from 0.002 to 0.02%, and the concentration of disodium dihydrate ethylenediaminetetraacetate is from 0.005 to 0.1%.

12. A method for inhibiting bacterial growth in an ophthalmic solution comprising a wound healing accelerator wherein the wound healing accelerator is fibronectin, epithelial growth factor, or fibroblast growth factor, and said ophthalmic solution is free of albumin, said method comprising adding to said ophthalmic solution a lower alkyl p-hydroxybenzoate preservative in an amount sufficient to inhibit bacterial growth in said ophthalmic solution, while preserving the wound healing properties of the wound healing accelerator.

* * * * *

UNITED STATES PATENT AND TRADEMARK OFFICE
CERTIFICATE OF CORRECTION

PATENT NO. : 5,514,647

DATED : May 7, 1996

INVENTOR(S): Bernard Horowitz, Richard W. Schulman, Adrianne J. Setton, Toyohiko Nishimura and Yoichi Kawashima It is certified that error appears in the above-identified patent and that said Letters Patent is hereby corrected as shown below:

```
   On title page, change "[62]  Division of Ser. No. 60,244" to
--[62]  Division of Ser. No. 60,224--.
```

Signed and Sealed this

Fifteenth Day of October, 1996

Attest:

BRUCE LEHMAN

*Attesting Officer*     *Commissioner of Patents and Trademarks*